(12) United States Patent
Nishi et al.

(10) Patent No.: US 6,620,421 B1
(45) Date of Patent: Sep. 16, 2003

(54) WATER DISPERSIBLE GRANULES

(75) Inventors: Shugo Nishi, Minoo (JP); Seiji Iuchi, Nishinomiya (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/676,485

(22) Filed: Oct. 2, 2000

(30) Foreign Application Priority Data

Oct. 5, 1999 (JP) .......................................... 11-283995

(51) Int. Cl.$^7$ ................................................ A01N 25/12
(52) U.S. Cl. ...................... 424/409; 424/405; 424/417; 424/418; 424/419; 424/420; 424/421
(58) Field of Search ................................. 424/405, 409, 424/417–421; 504/116, 118, 150; 523/122

(56) References Cited

U.S. PATENT DOCUMENTS

| | | | |
|---|---|---|---|
| 4,867,972 A | | 9/1989 | Girardeau et al. ............. 424/81 |
| 5,137,726 A | | 8/1992 | Ogawa et al. ............... 424/405 |
| 5,439,683 A | * | 8/1995 | Hodakowski ................ 424/408 |
| 5,945,114 A | | 8/1999 | Ogawa et al. ............... 424/408 |

FOREIGN PATENT DOCUMENTS

| | | |
|---|---|---|
| JP | 57-163303 | 10/1982 |
| JP | 2575009 | 10/1996 |
| WO | WO 96/36226 | 11/1996 |
| WO | WO 97/15186 | 5/1997 |

\* cited by examiner

*Primary Examiner*—Neil S. Levy
(74) *Attorney, Agent, or Firm*—Sughrue Mion, PLLC

(57) ABSTRACT

This invention relates to a water dispersible granule comprising;

(1) a pesticidally active ingredient
(2) a copolymer of maleic anhydride and diisobutylene or a salt thereof
(3) a compound selected from the group consisting of a polyoxyethylene alkyl phenyl ether Sulfuric acid ester, a polyoxyethylene aryl phenyl ether sulfuric acid ester, a polyoxyethylene alkyl phenyl other phosphoric acid ester, and a polyoxyethylene aryl phenyl ether phosphoric acid ester, or a salt thereof
(4) a water soluble carrier selected from the group consisting of water soluble polymers, succharides, and reduction products thereof sulfates, carbonates, phosphates, condensed phosphoric acids and salts thereof, solid organic acids, solid organic acid salts, protein, amino acids and a urea, and
(5) a water swellable material, The present composition is excellent in disintegration in water and storage stability, and after the storage for a long time, it keeps excellent property as water dispersible granules such as disintegration in water.

8 Claims, No Drawings

WATER DISPERSIBLE GRANULES

The present invention relates to a water dispersible granule.

Usually, a water dispersible granule is diluted with water and the dilution is applied to crops or the like. Therefore, it is demanded to have a high disintegrability in water and a high dispersibility in water. It is also demanded to have enough storage stability so that it keeps the enough disintegrability and the dispersibility after long term storage.

Until now, it was difficult to prepare a good water dispersible granule comprising a pesticidally active ingredient which was liquid, semi-solid or viscous, easily, because impossibility of granulation, difficulty of handling in preparation or the like arose. Therefore, it is demanded that one can prepare a good water dispersible granule comprising such pesticidally active ingredient which was liquid, semi-solid or viscous, easily.

The present inventors had studied extensively and then found that the following water dispersible granule has an excellent property as a Water dispersible granule and completed the present invention.

The present invention provides a water dispersible granules (hereinafter, referred to as the present composition) comprising:

(1) at least one pesticidally active ingredient (hereinafter, referred to as component (1))

(2) at least one compound selected from the following groups i) and ii)
  1) a copolymer of maleic anhydride and diisobutylene
  ii) an alkali metal salt, an alkali earth metal salt, an ammonium salt and an amine salt of the copolymer i)
  (hereinafter, referred to as component (2))

(3) at least one compound selected from the following groups iii) and iv)
  iii) a polyoxyethylene alkyl phenyl ether sulfuric acid ester, a polyoxyethylene aryl phenyl ether sulfuric acid ester, a polyoxyethylene alkyl phenyl ether phosphoric acid ester, and a polyoxyathylene aryl phenyl ether phosphoric acid ester
  iv) an alkali metal salt, an alkali earth metal salt, an ammonium salt and an amine salt of the compound of the group iii)
  (hereinafter, referred to as component (3))

(4) at least one water soluble carrier selected from the group consisting of water soluble polymers, succharides, and reduction products thereof, sulfuric acid salts, carboxylic acid salts, phosphoric acid salts, condensed phosphoric acids and salts thereof, solid organic acids, solid organic acid salts, protein, amino acids and a urea (hereinafter, referred to as component (4)), and (5) at least one water swellable material
  (Hereinafter, referred to as component (5)),
  and the weight ratio of the component (3) to the component (2) being 1/9 to 9.

By the combination of the components (1), (2), (3), (4) and (5), the present composition has an excellent disintegrability and dispersibility in water. The present composition has an excellent storage stability, therefore, after the storage for a long time, it keeps enough disintegrability in water and dispersibility in wager. Even though the pesticidally active ingredient as liquid, semi-solid or high viscosity, a satisfactory water dispersible granule can be obtained in the present invention.

The component (1), i.e. the pesticidally active ingredient used in the present invention comprises insecticidal active ingredients, an acaricidal active ingredients, fungicidal active ingredients, herbicidal active ingredients, plant growth regulators, insect growth regulators, and the like. The typical examples of the pesticidally active ingredient include the following compounds, and one or more geometrical isomers and optical isomers thereof.

Organophosphosphate Compounds

O,O-dimethyl O-(3-methyl-4-nitrophenyl) phosphorothioate. O,O-dimethyl O-[3-methyl-4-(methylthio)phenyl] phosphorothioate, O,O-diethyl O-(2-isopropyl-6-methylpyrimidin-4-yl) phosphorothioate, O,O-diethyl O-3,5,6-trichloro-2-pyridyl phosphorothloate, O,S-dimethylacetylphosphoramidothioate S-2,3-dihydro-5-methoxy-2-oxo-1,3,4-thiadiazol-3-ylmethyl O,O-dimethylphosphorodithioate, O,O-diethyl S-2-ethylthloothylphosphorodlthioate, 2,2-dichlorovinyldimethylphosphate, O-ethyl O-4-(methylthio) phenyl S-propylphosphorodithioate, O-4-cyanophenyl O,O-dimethylphosphorothioate, 2-methoxy-4H-1,3,2-benzodloxaphosphorin-2-sulfide, O,O-dimethyl S-(N-methylcarbamoylmethyl)dithlophosphate, ethyl 2-dimethoxyphosphtnothioylthio(phenyl)acetate, diethyl (dimethoxyphosphinothioylthio)succinate, dimethyl 2,2,2-trichloro-1-hydroxyethylphosphonate, S-3,4-dihydro-4-oxo-1,2,3-benzotriazin-3-ylmethyl O,O-dimethylphosphorothioate, dimethyl-[(E)-1-methyl-2-(methylcarbamoyl)vinyl]phosphate, O,O,O'O'-tetraethyl-S, S'-methylenebis(phosphorothioate), O-2,6-dichloro-4-methylphenyl O,O-dimethylphosphorothioate Carbamate Compounds 2-sec-butylphenyimethylcarbamate, ethyl N-[2,3-dihydro-2, 2-dimethylbenzofuran-7-yloxycarbonyl(methyl) aminothio]-N-isopropyl-β-alaninate 2-isopropoxyphenyl-N-methylcarbamate, 2,3-dihydro-2,2-dimethyl-7-benzo[b] furanyl N-dibutylaminothio-N-methylcarbanate, 1-naphthyl-N-methylcarbamate. S-methyl-N-(methylcarbamoyloxy)thioacetimidate, 2-(ethylthiomethyl) phenylmethylcarbamate, 2-methyl-2-(methylthio) proplonaldehyde O-methylcarbamoyloxime, N,N-dimethyl-2-methylearbamoyloxyimino-2-(methylthio)acetamide. S-4-phenoxybutyl-N,N-dimethylthiocarbamate Pyrethroid Compounds 2-(4-ethoxyphenyl)-2-methyl-1-(3-phenoxybenzyl) oxypropane, (RS)-α-cyano-3-phenoxybenzyl (RS)-2-(4-chlorophenyl)-3-methylbutyrate, (S)-α-cyano-3-phenoxybenzyl (S)-2-(4-chlorophenyl)-3-methylbutyrate, (RS)-α-cyano-3-phenoxybenzyl 2,2,3,3-tetramethylcyclopropanecarboxylate, (RS)-α-cyano-3-phenoxybenzyl (1RS)-cis,trans-3-(2,2-dichlorovinyl)-2,2-dimethylcyclopropanecarboxylate, 3-phenoxybenzyl (1RS)-cis,trans-3-(2,2-dichlorovinyl)-2,2-dimethylcyolopropanecarboxylate, (RS)-α-cyano-3-phenoxybenzyl (1RS,3Z)-c1s-3-(2-chloro-3,3,3-trifluoroprop-1-enyl)-2,2-dimethylcyclopropanecarboxylate, (S)-α-cyano-3-phenoxybenzyl (1R)-cis-3-(2,2-dibromovinyl)-2,2-dimethylcyclopropanecarboxylate, (RS)-α-cyano-3-phenoxybenzyl (RS)-2,2-dichloro-1-(4-ethoxyphenyl) cyclopropanecarboxylate, α-oyano-3-phenoxybenzyl N-(2-chloro-α,α,α-trifluoro-p-tolyl)-D-valinate, 2-methyl-3-phenylbenzyl (1RS,3Z)-cis-3-(2-chloro-3,3,3-trifluoro-1-propenyl)-2,2-dimethylcyclopropanecarboxylate, 2-(4-bromodifluoromethoxyphenyl)-2-methyl-1-(3-phenoxybenzyl)methylpropane, (S)-α-cyano-3-phenoxybenzyl (1R)-cis-3-(1,2,2,2-tetrabromoethyl)-2,2- dimethylcyclopropanecarboxylate, (4-ethoxyphenyl)-[3-(4-fluoro-3-phenoxyphenyl)propyl]dimethylasilane, 3-phenoxybenzyl (1(R)-cis,trans-2.2-dimethyl-3-(2-methyl-1-propenyl)cyclopropanecaboxylate, (RS)-α-cyano-3-phenoxybenzyl (1R)-cis,trans-2,2-dimethyl-3-(2-methyl-1-propenyl)cyclopropanecarboxylate, 5-benzyl-3-furylmethyl (1R)-cis,trans-2,2-dimethyl-3-(2-methyl-1-propenyl) cyclopropanecarboxylate, (S)-α-cyano-3-phenoxybenzyl (1R,3Z)-cis-(2,2-dimethyl-3-[3-oxo-3-(1,1,1,3,3,3-hexatfluoropropyloxy)propenyl]cyclopropanecarboxylate, (RS)-α-oyano-4-fluoro-3-phenoxybenzyl 3-(2,2-dichlorovinyl)-2,2-dimethylcyclopropanecarboxylate, 2,3,5,6-tetrafluoro-4-methylbenzyl (1RS,3Z)-cis-3-(2-chloro-3,3,3-trifluoro-1-propenyl)-2,2-dimethylcyclopropanecarboxylate, 2,3,5,6-tetrafluorobenzyl (1R)-trans-3-(2,2-dichlorovinyl)-2,2-dimethylcyclopropanecarboxylate, 3,4,5,6-tetrahydrophthalimidomethyl (1RS)-cis,trans-2,2-dimethyl-3-(2-methyl-1-propenyl)cyclopropanecarboxylate, (RS)-2-methyl-4-oxo-3-(2-propenyl)-2-cyclopenten-1-yl (1RS)-cis,trans-2,2-dimethyl-3-(2-methyl-1-propenyl) cyclopropanecarboxylate, (S)-2-methyl-4-oxo-3-(2-propynyl)-2-cyclopenten-1-yl (1R)-cis,trans-2,2-dimethyl-3-(2-methyl-1-propenyl)cyclopropanecarboxylate, (RS)-1-ethynyl-2-methyl-2-pentenyl (1R)-cis,trans-2,2-dimethyl-3-(2-methyl-1-propenyl)cyclopropanecarboxylate, 2,5-dioxo-3-(2-propynyl)imidazolidin-1-ylmethyl (1R)-cis,trans-2,2-dimethyl-3-(2-methyl-1-propenyl) cyclopropanecarboxylate, 5-(2-propynyl)furfuryl (1R)-cis,trans-2,2-dimethyl-3-(2-methyl-1-propenyl) cyclopropanecarboxylate, 5-(2-propynyl)furfuryl 2,2,3,3-tetramethylcyclopropanecarboxylate Phosphorylated Amino Acid Compounds N-phosphonomethylglycine, agriculturally acceptable salt thereof, 4-hydroxymethylphosphinoyl-L-homoalanyl-L-alanine Thiadiazlne Derivatives 3-isopropyl-1H-2,1,3-benzothiadiazin-4(3H)-on 2,2-dioxide, 2-tert-butylimino-3-isopropyl-5-phenyl-1,3,5-thiadlazin-4-one Nitroimidazolidine Derivatives Nereistoxln Derivatives S,S'-(2-dimethylaminotrimethylene)bis(thiocarbamate), N,N-dimethyl-1,2,3-trithian-5-ylamine, S,S'-2-dimethylaminotrimethylene di(benzenethiosulfonate)

N-Oyanoamidine Derivatives

N-cyano-N'-methyl-N'-(6-chloro-3-pyridylmethyl) acetamidine

Chlorinated Hydrocarbon Compounds 6,7,8,9,10,10-hexachloro-1,5,5a,6,9,9a-hexahydro-6,9-methano-2,4,3-benzodioxathiepineoxide, 1,2,3,4,5,6-hexachlorocyclohexane, 1,1-bis(4-chlorophenyl)-2,2,2-trichloroethanol Benzoylphenylurea Compounds 1-[3,5-dichloro-4-(3-chloro-5-trifluoromethylpyridin-2-yloxy)phenyl]-3-(2,6-difluorobenzoyl)urea, 1-(3,5-dichloro-2,4-difluorophenyl)-3-(2,6-difluorobenzoyl)urea, 1-[4-(2-chloro-4-trifluoromethylphenoxy)-2-fluorophenyl]-3-(2,6-difluorobenzoyl)urea Formamidlne Derivatives N,N'-[(methylimino)dimethylidine]-di-2,4-xylidine, N'-(4-chloro-2-methylphenyl)-N,N-dimethylmethynimidamide, Thiourea Derivatives N-(2,6-diisopropyl-4-phenoxyphenyl)-N'-t-butylcarbodiimide N-Phenylpyrazole 5-methoxy-3-(2-methoxyphenyl)-1,3,4-oxadiazol-2-(3H)-one, isopropyl 4,4'-dibromobenzypate, 4-chlorophenyl 2,4,5-trichlorophenylsulfone, S,S-6-methylquinoxalin-2,3-diyldithiocarbonate, 2-(4-tert-butylphenoxy) cyclohexylprop-2-ylsulfite, bis[tris(2-methyl-2-phenylpropyl)tin]oxide, (4RS,5RS)-5-(4-chlorophonyl)-N-chlorophenyl)-N-chlorohexyl-4-methyl-2-oxo-1,3-thiazolidine-3-carboxamide, 3,6-bis(2-chlorophenyl)-1,2,4,5-tetrazine, 2-tert-butyl-5-(4-tert-butylbenzylthio)-4-chloropyridazin-3(2H)-one, tert-butyl (E)-4-[(1,3-dimethyl-5-phenoxypyrazol-4-yl)methyleneaminooxymethyl] benzoate, N-4-tert-butylbenzyl-4-chloro-3-ethyl-1-methyl-5-pyrazolecarboxamide, tetranactin, dinactin, trinactin, 5-chloro-N-[2-[4-(2-ethoxyethyl)-2,3-dimethylphenoxy] ethyl]-6-ethylpyrimidin-4-amine], milbemectin, abamectin, ivermectin, azadirachtin [AZAD], 5-methyl[1,2,4]triazolo [3,4-b]benzothlazole, methyl 1-(butylcarbamoyl) benzimidazol-2-carbamate, 6-(3,5-dichloro-4-methylphenyl)-3(2H)-pyridazinone, 1-(4-chlorophenoxy)-3,3-dimethyl-1-(1H-1,2,4-triazol-1-yl)butanone, (E)-4-chloro-2-(trifluoromethyl)-N-[1-(imidazol-1-yl)2-propoxyethylidene]aniline, 1-[N-propyl-N-[2-(2,4,6-trichlorophenoxy)ethyl]carbamoyl]imidazole, (E)-1-(4-chlorophenyl)-4,4-dimethyl-2-(1H-1,2,4-triazol-1-yl)-1-penten-3-ol, -1-(4-chlorophenyl)-4,4-dimethyl-2-(1H-1,2,4-triazol-1-yl)pentan-3-ol, (E)-1-(2,4-dichlorophenyl)-4,4-dimethyl-2-(1H-1,2,4-triazol-1-yl)-penten-3-ol, 1-(2,4-dichlorophenyl)-4,4-dimethyl-2-(1H-1,2,4-triazol-1-yl) pentan-3-ol, 4-[3-(4-tert-butylphenyl)-2-methylpropyl]-2,6-dimethylmorpholine, 2-(2,4-dichlorophenyl)-1-(1H-1,2,4-triazol-1-yl)hexan-2-ol, O,O-diethyl O-2-quinoxalinyl phosphorothioate, O-(6-ethoxy-2-ethyl-4-pyrimidinyl) O,O-dimethyl phosphorothioate, 2-diethylamino-5,6-dimethylpyrimidin-4-yl dimethylcarbamate, 4-(2,4-dichlorobenzoyl)-1,3-dimethyl-5-pyrazolyl p-toluenesulfonate, 4-amino-6-(1,1-dimethylethyl)-3-methylthio-1,2,4-triazin-5(4H)-one, 2-chloro-N-[(4-methoxy-6-methyl-1,3,5-triazin-2-yl)aminocarbonyl] benzenesulfonamide, 2-methoxycarbonyl-N-[(4,6-dimethoxypyrimidin-2-yl)aminocarbonyl] benzenesulfonamide, 2-methoxycarbonyl-N-[(4,6-dimethylpyrimidin-2-yl)aminocarbonyl] benzenesulfonamide, 2-methoxycarbonyl-N-[(4-methoxy-6-methyl-1,3,5-triazin-2-yl)aminocarbonyl] benzenesulfonaminde, 2-ethoxycarbonyl-N-[(4-chloro-6-methoxypyrimidin-2-yl)aminocarbonyl] benzenesulfonamide, 2-(2-chloroethoxy)-N-[(4-methoxy-6-methyl-1,3-5-triazin-2-yl)aminocarbonyl] benzenesulfonamide, 2-methorycarbonyl-N-1(4,6-dimethoxypyrimidin-2-yl)aminocarbonyl] phenylmethanesulfonamide, 2-methoxycarbonyl-N-[(4-methoxy-6-methyl-1,3,5-triazin-2-yl)aminocarbonyl] thiophene-3-sulfonamide, 4-ethoxycarbonyl-N-[(4,6-dimethoxypyrimidin-2-yl)aminocarbonyl]-1-methylpyrazole-5-sulfonamide, 2-[4,5-dihydro-4-methyl-4-(1-methylethyl)-5-oxo-1H-imidazol-2-yl]-3-quinolinecarboxylic acid, 5-ethyl-5,8-dihydro-8-oxo[1,3] dioxoro[4,5-g]quinoline-7-carboxylic acid, 2-[4,5-dihydro-4-methyl-4-(1-methylethyl)-5-oxo-1H-imidazol-2-yl]-5-ethyl-3-pyridinecarboxylic acid, methyl 6-(4-isopropyl-4-methyl-5-oxoimidazolin-2-yl)-m-toluate, methyl 2-(4-isopropyl-4-methyl-5-oxoinidazolin-2-yl)-p-toluate, 2-(4-isopropyl-4-methyl-5-oxoimidazolin-2-yl)nicotinio acid, N-(4-chlorophenyl)methyl-N-cyclopentyl-N'-phenylurea, (RS)-2-cyano-N-[(R)-1-(2,4-dichlorophenyl)ethyl]-3,3-dimethylbutylamide, N-(1,3-dihydro-1,1,3- trimethylisobenzofuran-4-yl)-5-chloro-1,3-dimethylpyrazole-4-carboxyamide, N-[2,6-dibromo-4-(trifluoromethoxy)phenyl]-2-methyl-4-(trifluoromethyl)-5-thiazolcarboxyamide, 2,2-dichloro-N-[1-(4-chlorophenyl)ethyl]-3-methylcyclopropanecarboxyamide, methyl (E)-2-2-6-(2-cyanophenoxy)pyrimidin-4-yloxy-phenyl-3-methoxyacrylate, 5-methyl-1,2,4-triazolo[3,4-b]benzothiazole, 3-allyloxy-1,2-benzcisothiazol-1,1-dioxide, diisopropyl 1,3-dithiolan-2-yliden-malonate, O,O-dipropyl O-4-methylthiophenylphosphate, etc.

The component (1) (i.e. pesticidally active ingredient) maybe comprised in an amount of 1 to 75% by weight, preferably, 3 to 60% by weight, and more preferably, 5 to 40% by weight, in the present composition.

As the component (2), one or more compound selected from the group consisting of a copolymer of maleic anhydride and diisobutylene, and an alkali metal salt (ex. a sodium salt, a potassium salt), an alkali earth metal salt (ex. a calcium salt, a magnesium salt), an ammonium salt (ex. ammonium salt, alkyl trimethyl ammonium salt), and an amine salt (ex. a triethanolamine salt thereof are contained in the present composition. The mean molecular weight of the copolymer may be raging from 500 to 50,000, for example.

As the component (3), one or more compound selected from the group consisting of the following compounds are used. Sulfuric acid esters consisting of a polyoxyethylene alkyl phenyl ether sulfurlc acid ester (ex. a polyoxyethylene nonyl phenyl ether sulfuric acid ester), and a polyoxyathylene aryl phenyl ether sulfuric acid ester (ex. a polyoxyethylene styryl phenyl ether sulfuric acid ester, a polyoxyethylene distyryl phenyl ether sulfuric acid ester, a polyoxyethylene tristyryl phenyl ether sulfuric acid ester);

phosphoric ac&d esters consisting of a polyoxyethylene alkyl phenyl ether phosphoric acid ester (ex. a polyoxyothylene nonyl phenyl ether phosphoric acid ester), and a polyoxyethylene aryl phenyl ether phosphoric acid ester (ex. a polyoxyethylenestyryl phenyl ether phosphoric acid ester, a polyoxyethylenedistyryl phenyl ether phosphoric acid ester, a polyoxyethylenetristyryl phenyl ether phosphoric acid ester);

an alkali metal salt (ex. a sodium salt, a potassium salt), an alkali earth metal salt (ex. a calcium salt, a magnesium salt, an ammonium salt, an amine salt (ex. triethanolamine salt) of the above sulfuric acid esters and the above phosphoric acid esters when the sulfuric acid ester is a sulfuric acid mono ester, or the phosphoric acid ester is a phosphoric acid mono ester or a phosphoric acid diester; (wherein the carbon atom number of the alkyl part of the polyoxyethylene alkyl phenyl ether sulfuric acid ester and the polyoxyethylen alkyl phenyl ether phosphoric acid ester may be 2 to 25, and the carbon atom number of the aryl part of the polyoxybthylene aryl phenyl ether sulfuric acid ester and polyoxyethylene aryl phenyl ether phosphoric acid ester may be 6 to 40, for example)

The weight ratio of the component (3) to the component (2) is 1/9 to 9. The component (2) and the component (3) may be contained in total amount of 3 to 30% by weight, preferably 5 to 20% by weight, more preferably 6 to 15% by weight in the present composition.

The component (4), i.e. a water soluble carrier is one or more compounds selected from the group consisting of water soluble polymers such as polyvinylalcohol and polyvinylpyrrolidone; succharides, and reduction products thereof such as monosaccharide or disaccharide (ex. glucose, lactose, fructose, maltose, sucrose), reducting sugar (ex sorbitol, multitol, reduced lactose, soluble modified starch (ex. dextrin, soluble starch oxidated starch); sulfuric acid salts such as alkal metal salts, alkali earth metal salts, ammonium salts and amine salts (ex, ammonium sulfate; carboxylic acid salts such as alkali metal salts, alkali earth metal salts, ammonium salts and amine salts (ex, sodium carbonate; phosphoric acid salts such as alkal metal salts, alkali earth metal salts, ammonium salts and amine salts (ex, sodium phosphate; condensed phosphoric acids and salt thereof such as an alkali metal salts, an alkali earth metal salt, an ammonium salt, an amine salt of pyrophosphoric acid and tripolyphosphoric acid; solid organic acids such as citric acid, succinic acids fumaric acid, malic acid and ascorbic acid; solid organic acid salts such as sodium citrate; protein such as gelatin and casein; amino acids such as sodium glutamate and a glycine; and a urea. Among them, preferable are Succharides, and more preferable are mono- or di-succharides. Among them, more preferable is sucrose. Among the sucrose, fine sucrose powder to pass through 200 mesh sieve is preferable. The fine sucrose powder may be obtained by pulverizing with a pulverizer. The commercially available product such as High grade powder sugar (produced by Nissin Sugar Manufacturing Co., Ltd) may be used.

The water soluble carrier may be contained in an amount of 2 to 90% by weight, preferably 10 to 80% by weight, more preferably 15 to 60% by weight in the present composition.

The component (5), i.e. a water swellable material is one which swells in the presence of water. The water swellable materials comprises microbial polysaccharides such as xanthan gum, and rhamsan gum; cellulose derivatives such as crystal cellulose, hydroxymethylcellulose, hydroxypropylcellulose, hydroxypropylmethylcellulose, methylethylcellulose, methylcellulose, sodium carboxymethylcellulose, calcium carboxymethylcellulose, cross-linking water soluble synthetic polymer such as cross-linking polyvinylpyrrolidone; water swellable clays such as montmorillonite, laponite, bentonite, smectite, and vee-gum®. Among them, the water swellable clays are preferable. When sucrose is used as the component (4), it is especially preferable to use water swellable clays, and among them, bentonite is more preferable.

The water swellable material may be contained in an amount of 0.1 to 40% by weight, preferably 0.5 to 30% by weight, more preferably 1 to 20% by weight in the present invention.

The present composition may be contain water insoluble carriers, surfactants, solvents, if necessary.

The water insoluble carriers comprises precipitated silica such as Tokusil (trade name of Tokuyama Co., Ltd.), Carplex® (trade name of Shlonogi & Co., Ltd.), Wessalon (trade name of Degussa Co.), Sipernat (trade name of Degussa Co.); fumed silica such as Aerosil (trade name of Degussa Co.); and mineral carriers such as kaolin, diatomaceous earth, calcined diatomaceous earth, talc, calcium carbonate, terra alba and attapalgite.

The water insoluble carriers may be used solely or in combination with two or more, and may be contained in an amount of 70% by weight or less, preferably 50% by weight or less in the present composition.

The surfactants comprise nonionic surfactants, anionic surfactants, cationic surfactants, amphoteric surfactants, and mixtures thereof. The nonionic surfactants and/or the anionic surfactants are usually used.

The nonionic surfactants comprise polyoxyethylenecaroxylate, polyoxyethylene polyoxypropylene alkyl aryl ether, polyoxysthylene polyoxypropylene block copolymer, polyoxysthylenealkyl aryl ether, polyoxyathylene alkyl ether, polyoxyethylenepolyoxypropylenetristyryl phenyl ether, polyoryothylenestyryl phenyl ether, polyoxyethylenetristyryl phenyl ether, polyoxyethylene fatty acid ester, fatty acid ester, polyol fatty acid ester, polyoxyethylene polyol fatty acid ester, polyoxyethylenealkyl amine, and the like. The anionic surfactants comprise dialkylsulfocarboxylate, alkylsulfate. alkylaryl sulfonate, polycarboxylate, alkylnaphthalenesulfonate, metal salt of naphthalenesulfonlc acid polycondensate, alkenylsulfonate, naphthalenesulfonic acid formalin condensate, dialkylsuocisulfonate, ligninsulfonate, and the like.

The surfactant can be used solely or in combination with two or more surfactants, and may be comprised in an amount of generally 40% by weight or less, preferably 20% by weight or less, more preferably 10% by weight or less in the present composition.

The solvents comprise paraffin solvents, aromatic solvents, polar solvents, animal/vegetable oils, and the like.

The paraffin solvents comprise normal paraffin, isoparaffin, cycloparaffin, and the like. The aromatic solvents comprise xylene, alkylbenzene, alkylnaphthalene, phenylxylylethane, diphenylxylylethane, and the like. The polar solvents comprise ketones such as cyclohexanone, heptanone, octanone, nonanone, N-methylpyrrolidone, acetophenone; eaters such as hexyl acetate, benzyl acetate, phenylethylacetate, benzyl benzoate, methyl benzoate, isobutyl oleate, benzyl sallcylate, butylcycloheyl acetate, methylbenzyl acetate, methyl oleate, methyl laurate and alkylenedicarboxylic acid mono- or di-esters (ex. a mixture of dibasic acid ester having 2 to 4 ethylene groups, diisodecyl phthalate, dioctyl phthalate, diisodecyl adipate, diisobutyl adipater alcohols such as ethylene glycol, propylene glycol, benzyl alcohol, phenylethyl alcohol, butylcyclohexanol, phenyloxy ethanol. The animal/vegetable oils comprise rape seed oil, soybean oil, linseed oil, and the like.

The solvents can be used solely or in combination with two or more solvents. Among them, preferable are the solvents having a flashing point of 100° C. or higher, and more preferable are the solvents having a flashing point of 150° C. or higher. The amount of the solvents may be determined suitably in view of the reason of use of the solvents such as for easy handling of the making the composition, for preventing crystal deposits in preservation under low temperature, for adjusting the effect and for controlling the viscosity of the pesticidally active ingredient.

When the component (1) (i.e. pesticidally active ingredient) is solid at the normal temperature, the solvent may be comprised in an amount of generally 40% by weight or less, preferably 30% by weight or less, more preferably 20% by weight or less in the present composition. When the component (1) is liquid or semi-solid at the normal temperature, the solvent may be comprised in an amount of generally 50% by weight or less, preferably 30% by weight or less, more preferably 20% by weight or less in the present composition.

When the present composition comprises solvent and/or the component (1) which is liquid at the normal temperature, it is preferable that the above-mentioned water insoluble carrier such as precipitated silicas fumed silica and attapalgite is used, because it operates as a support of the liquid component in the present composition. Among them, more preferable is the water insoluble carrier having a high oil absorption ability, for example, one having BET surface area of 250 or more such as SIPERNAT 50S (trade name: wet silica produced by Degussa Co.). The water insoluble carrier may be comprised in a ratio of generally 10 to 300 parts by weight, preferably 20 to 170 parts by weight to 100 parts by weight of the liquid component (total amount of the solvent and/or the component (1) dissolved in the solvent and/or liquid component (1)).

The present composition may be comprise hydrophobic materials or water-repellent materials (hereinafter, referred to as hydrophobic/water-repellent materials) for the purpose of the reduction of sedimentation in water or improvement of the dispersion speed when it is added into water.

Typical examples of the hydrophobic/water-repellent materials are solids materials including fatty acid having 10 or more carbon atoms such as capric acid, laurie acid, stearic acid and oleic acid; metal salts of fatty acid such as calcium stearate, magnesium stearate, sodium stearate, zinc stearate, aluminum stearate and barium stearate; powdery paraffin; kinds of wax: hydrophobic silica (ex, Aerosil R972. Aerosil R974, Aerosil R976 (all product by Degussa Co., Ltd.); and liquid materials including fatty acids having 6 to 9 carbon atoms such as oaproic acid, caprylic acid and pelargonic acid; higher alcohol such as oleyl alcohol and stearyl alcohol: liquid paraffin; naphthene; and silicone oil and derivatives thereof.

The hydrophobic/water-repellent material may be contained in an amount of generally 10% by weight or less in the present composition. The hydrophobic/water-repellent material may be contained in the present composition by mixing with the other components generally. When the hydrophobic/water-repellent material is liquid, it is practically preferable that the material is absorbed in powders such as the component (5) (i.e. swellable material, water insoluble carrier and the like, and then, mixed are the powder absorbing the material and the other components.

The present composition further comprises additives such as preservatives, binders, stabilizer, Enhancer of biological activity, colarant, perfume, lubricant and the like.

The method for producing the present composition includes dry granulation method, wet extruding granulation method, spray-drying granulation method, fluidized bed granulation method and the like. Among them, the wet extruding granulation method, spay-drying granulation method and fluidized bed granulation method are preferable, and the wet extruding granulation method is more preferable. The typical wet extruding granulation method are explained below.

When the component (1) (i.e, pesticidally active ingredient) is solid, it is pulverized by dry pulverizer such as pin mill, hammer mill, ball mill, jet mill and the like. In the pulverized material obtained, the component (2), the component (3), the component (4) and the component (5), if necessary, the solvent, surfactant, water insoluble carrier and/or the other additives are added and mixed with mixer such as ribbon mixer, Nauta mixer and the like. All or a part of the components other than the component (1) may be mixed with unpulverized pesticidally active ingredient, previously, and then the mixture may be pulverized. The obtained mixture is added with water in an amount of about 5 to 30% by weight based on the weight of the mixture and kneaded with pestle and mortar, Nauta mixer, kneader and the like. The kneaded is granulated with granulator such as Basket Granulator, Twin-Dome Gran (produced by Fuji Paudal Co., Ltd.) to form granules. An opening diameter of the screen used in granulation is generally about 0.3 to 2 mm, and from the view point of industrial production, is preferably about 0.5 to 1.5 mm. The diameter of the granules obtained is generally about 0.01 to 3 mm, and from the view point of industrial production, is preferably about 0.05 to 2 mm. Finally, the granules are dried with dryer such as fluidized bed dryer at room temperature to 150° C. to give the present composition.

When the component (1) (i.e. pesticidally active ingredient) is liquid, the ingredient, which is added with the solvent to be a solution if necessary, is mixed with the component (5) (i.e. water swellable material) or the water insoluble carrier by mixer such as ribbon mixer. Nauta mixer and the like, and then, pulverized with dry pulverizer such as pin mill, hammer mill and the like. In this case, the amount of the component (5) or the water insoluble carrier may be 10 to 300 parts by weight, preferably 20 to 170 parts by weight based on 100 parts by weight of the component (1) or the solution thereof. To the pulverized, the component (2), component (3), component (4), and if necessary the component (5), solvent, surfactant, water insoluble carrier and other additives, are added and then mixed by mixer above mentioned. All or a part of the components which are mixed after the above pulverization may be mixed before the pulverization. The mixture obtained can be formulated to be the present composition by kneading, granulating and drying as well as the case in which the component (1) is solid.

When the component (1) (i.e. pesticidally active ingredient) is semi-solid, the present composition can be obtained by conducting same method as one in case the component (1) is liquid after the component (1) is made to be liquid by adding the solvents or heating it.

The present composition is used for controlling posts such as insects, acarina, fungi and weeds or regulating plant growth and the like. The present composition is diluted with water and the dilution may be applied to crops or soil by sprayer or the like. The dilution ratio of the present composition is generally about 10 to 10,000 times, preferably about 50 to 8,000 times, and more preferably about 500 to 4,000 times, although it varies depending upon the kind of the pesticidally active ingredient therein, the amount of the pesticidally active ingredient therein, the target for controlling or regulating, the place of application, the timing of application and the like.

The present composition may be contained in a container which is usable for usual granules or wettable powders such as aluminum bag, paper bag, paper pack and the like. Preferable are aluminum bags, and pager bags and polybags having aluminum coating therein in order to prevent the moisture absorption in storage. Also, the present composition may be packed in a water soluble pack and then may be contained in the above bags in expectation of the prevention of the moisture absorption in storage, the improvement of safety, and the improvement of usability in dilution.

This invention is explained more in detail with the following Examples, although the present invention is not limited to the Examples.

The test methods used in the Test Examples are explained below.

Disintearation Test in Water

In a 250-ml measuring cylinder having a stopper, 250 ml of 3° hard water of Japanese Official Analyzing Method (i.e. 19.2 ppm hard-water calculated as $CaCO_3$ which is diluted the CIPAC standard water D) is added and then, it is put in the water bath thermostat controlled at 20±1° C. to become 20° C. in the cylinder, 500 mg of each composition to be tested is put and the cylinder is turned upside down at a rate of 1 time per second. The necessary numbers of times are examined for perfect disintegration and dispersion of the composition. The composition tested is evaluated as follows.

| Necessary numbers of times | Evaluation |
| --- | --- |
| 10 to 14 | ⊚ |
| 15 to 19 | ○ |
| 20 to 24 | Δ |
| 25 to 29 | X |
| 30 or more | XX |

Accelerated Preservation Test

Each composition to put in an aluminum bag and the aluminum bag is sealed The aluminum bag is kept in a thermostat at 54±20° C. for 2 weeks.

Production Example 1

9.2 Parts by weight of (RS)-α-oyano-3-phenoxybenzyl (1RS)-cis, trans-3-(2,2-dicholorovinyl)-2,2-dimetyhylcyclopropanecarboxylate and 10 parts by weight of Hisol SAS-296 (phonyixylylethane; organic solvent manufactured by Nisseki Kagaku K.K) was mixed and heated at about 50° C. The mixture solution was added to 10 parts by weight of SIPERNAT 50S (white carbon manufactured by Degussa Co.) and mixed uniformly and pulverized by juicer mixer to be fine powders. To the fine powders, 8 parts by weight of the mixture of copolymer of maleic anhydride and diisobutylene and potassium salt of polyoxyethylenearyl phenyl ether sulfuric acid ester (Geropon SC-213; surfactant produced by Rhodia), 2 parts by weight of sodium dodecylbenzenesulfonate, 10 parts by weight of bentonite and 50.8 parts by weight of lactose are added, and mixed and pulverized by juicer mixer to obtain 200 g of mixed powders. The mixed powder was put in a mortar and ion exchanged water was added thereto in the ratio of 14 parts by weight based on 100 parts by weight of the mixed powder, mixed and kneaded with pastle. The kneaded was granulated by Single-Dome Gran (extrusion granulator manufactured by Fuji Paudal Co., Ltd.) attached with 0.5 mm φ screen, dried at 50° C. for 20 minutes and sieved to obtain water dispersible granules having a diameter of 300 to 710 μm. (Hereinafter, referred to as composition 1)

Comparative Production Example 1

9.4 Parts by weight of (RS)-α-cyano-3-phenoxybenzyl (1RS)-cis, trans-3-(2,2-dicholorovinyl)-2,2-dimethylcyolopropanecarboxylate and 10 parts by weight of Hisol SAS-296 (phenylxylylethane; organic solvent manufactured by Nisseki Kagaku K.K.) was mixed and heated at about 50° C. to be a mixed solution. On the other hand, 18 parts by weight of SIPERNAT 22S (white carbon manufactured by Degussa Co.), 5 parts by weight of sodium salt of alkylnaphthalens sulfonic acid formaldehyde condensate, 15 parts by weight of the mixture of alkylallylsulfonate, inorganic salt of phosphoric acid and white carbon, 10 parts by weight of bentonite and 32.6 parts by weight of lactose are mixed in a bag. Three hundred grams of the mixture was put in a high speed mixer, the mixed solution obtained previously was added by stirring and pulverized for 5 minutes. The powders obtained was put in a mortar, water was added thereto in a ratio of 15 parts by weight based on 100 parts by weight of the powders and then, the resultant was mixed and kneaded. The kneaded was granulated with Single-Dome Gran (extrusion granulator manufactured by Fuji Paudal Co, Ltd.) attached with 0.5 mm φ screen, dried at 50° C. for 10 minutes and sieved to obtain water dispersible granules having a diameter of 250 to 1,180 μm (Hereinafter, referred to as comparative composition 1)

Comparative Production Example 2

Water dispersible granules having a diameter of 250 to 1.180 μm was prepared in the same manner as the Comparative Production Example 1 except that the mixture of alkylsulfate and mirabilite was used instead of the mixture of alkylallylsulfonate, inorganic salt of phosphoric acid and white carbon. (Hereinafter, referred to as comparative composition 2)

Comparative Production Example 3

Water dispersible granules having a diameter of 250 to 1.180 μm was prepared in the same manner as the Comparative Production Example 1 except that dioctylsulfosuccinate was used instead of the mixture of alkylallylsulfonate, inorganic salt of phosphoric acid and white carbon. (Hereinafter, referred to as comparative composition 3)

Test Example 1

The disintegration test in water was conducted on the composition 1 and comparative compositions 1, 2 and 3, respectively. (Firet evaluation)

Further, on the composition having the first evaluation being "⊚" or "○", the accelerated preservation test was conducted and then, the disintegration test in water was conducted. (Second evaluation)

The results are shown in Table 1.

TABLE 1

| Composition tested | First evaluation | Second evaluation |
|---|---|---|
| composition 1 | ⊚ | ○ |
| comparative composition 1 | XX | — |
| comparative composition 2 | X | — |
| comparative composition 3 | XX | — |

Production Example 2

Water dispersible granules having a diameter of 300 to 710 μm was prepared in the same manner as the Production Example 1 except that the amounts of the bentonite and lactose were changed to 20 parts by weight and 40.8 parts by weight , respectively. (Hereinafter, referred to as composition 2)

Comparative Production Example 4

Water dispersible granules having a diameter of 300 to 710 μm was prepared in the same manner as the Production Example 2 except that bentonite was not used and the amount of lactose was changed to 60.8 parts by weight. (Hereinafter, referred to as comparative composition 4)

Test Example 2

The disintegration test in water was conducted on the composition 2 and comparative compositions 4, respectively. (First evaluation)

Further, on the composition having the first evaluation being "⊚" or "○", the accelerated preservation test was conducted and then, the disintegration test in water was conducted. (Second evaluation)

The results are shown in Table 2.

| Composition tested | First evaluation | Second evaluation |
|---|---|---|
| composition 2 | ⊚ | ⊚ |
| comparative composition 4 | ⊚ | Δ |

Production Example 3

Water dispersible granules having a diameter of 300 to 710 μm was prepared in the same manner as the Production Example 1 except that sucrose was used instead of lactose and the amount of the ion exchanged water was changed to 9 parts by weight. (Hereinafter, referred to as composition 3)

Comparative Production Example 5

When the same manner as the Production Example 3 was conducted except that bentonite was not used, the amount of sucrose was changed to 60.8 parts by weight and the amount of ion exchanged water was changed to 8 parts by weight or 12 parts by weight, water dispersible granules could not be obtained because of the impossibility of granulation.

Production Example 4

Water dispersible granules having a diameter of 300 to 710 μm was prepared in the same manner as the Production Example 3 except that 2 parts by weight of calcium stearate and 48.8 parts by weight of sucrose were used instead of 50.8 parts by weight of sucrose. (Hereinafter, referred to as composition 4)

Production Example 5

Water dispersible granules having a diameter of 300 to 710 μm was prepared in the same manner as the Production Example 1 except that the amounts of (RS)-α-cyano-3-phenoxybenzyl (1RS)-cis, trans-3-(2,2-dicholorovinyl)-2,2-dimethylcyclopropanecarboxylate and the ion exchanged water were changed to 9.4 parts by weight and 13 parts by weight, respectively, 15 parts by weight of potassium pyrophosphate and 35.6 parts by weight of kaolin were used instead of 50.8 parts by weight of lactose, and the temperature for drying was changed to 60° C. (Hereinafter, referred to as composition 5)

Comparative Production Example 6

When the same manner as the Production Example 5 was conducted except that bentonite was not used and the amount of ion exchanged water was changed to 28 parts by weight, water dispersible granules could not be obtained because of the impossibility of granulation. Although 5 parts by weight of the ion exchanged water was further added, water dispersible granules could not obtained because of the impossibility of granulation.

Test Example 3

The disintegration test in water was conducted on the compositions 3, 4 and 5, respectively. (First evaluation)

Further, on the composition having the first evaluation being "⊚" or "○", the accelerated preservation test was conducted and then, the disintegration test in water was conducted. (Second evaluation)

The results are shown in Table 3.

TABLE 3

| Composition tested | First evaluation | Second evaluation |
|---|---|---|
| composition 3 | ⊚ | ⊚ |
| composition 4 | ⊚ | ⊚ |
| composition 5 | ⊚ | ⊚ |

Production Example 6

Water dispersible granules having a diameter of 300 to 850 μm was prepared in the same manner as the Production Example 3 except that Basket Granulator (a granulator manufactured by Hata Tekkosyo) attached with 0.7 mm φ screen was used instead of Single-Dome Gran (extrusion granulator manufactured by Fuji Paudal Co. Ltd.) attached with 0.5 mm φ screen, and each component was used so that the amount of the mixture before granulation to be 1.5 Kg.

Production Example 7

Water dispersible granules having a diameter of 300 to 710 μm is prepared in the some manner as the Production Example 3 except that 2 parts by weight of copolymer of maleic anhydride with diisobutylene (Geropon T-36; surfactant produced by Rhodia) and 7 parts by weight of ammonium salt of polyoxyethylone di(1-phenylethyl)phenyl ether sulfuric acid ester (Soprophor DSS-11: surfactant produced by Rhodia) are used in stead of 8 parts by weight of the mixture of copolymer of maleic anhydride and duisobutylene and potassium salt of polyoxyethylenearyl phenyl ether sulfuric acid ester (Geropon SC-213; surfactant produced by Rhodia), and the amount of the sucrose is changed to 49.8 parts by weight.

Production Example 8

Water dispersible granules having a diameter of 300 to 710 μm is prepared in the same manner as the Production Example 3 except that 8 parts by weight of copolymer of maleic anhydride with dulsobutylene (Garopon T-36; surfactant produced by Rhodia) and 2 parts by weight of ammonium salt of polyoxyothylene di(1-phenylethyl) phenyl ether sulfuric acid ester (Soprophor DSS-7; surfactant produced by Rhodia) are used in stead of 8 parts by weight of the mixture of copolymer of maleic anhydride and diisobutylone and potassium salt of polyoxyethylenearyl phenyl ether sulfuric acid ester (Geropon SC-213; surfactant produced by Rhodia), and the amount of the sucrose is changed to 48.8 parts by weight.

The present composition is excellent in disintegration in water and storage stability, and after the storage for a long time, it keeps excellent property as water dispersible granules such as disintegration in water.

What is claimed is:

1. A water dispersible granule comprising:
   (1) at least one pesticidally active ingredient
   (2) at least one compound selected from the following groups i) and ii)
      i) a copolymer of maleic anhydride and duisobutylene
      ii) an alkali metal salt, an alkali earth metal salt, an ammonium salt and an amine salt of the copolymer i)
   (3) at least one compound selected from the following groups iii) and iv)
      iii) a polyoxyethylene alkyl phenyl ether sulfuric acid ester, a polyoxyethylene aryl phenyl ether sulfuric acid eater, a polyoryethylene alkyl phenyl ether phosphoric acid ester, and a polyoxyethylene aryl phenyl ether phosphoric acid ester
      iv) an alkali metal salt, an alkali earth metal salt, an ammonium salt and an amine salt of the compound of the group iii)
   (4) at least one water soluble carrier selected from the group consisting of water soluble polymers, succharides, and reduction products thereof, sulfates, carbonates, phosphates, condensed phosphoric acids and salts thereof, solid organic acids, solid organic acid salts, protein, amino acids and a urea, and
   (5) at least one water swellable material, and the weight ratio of the component (3) to the component (2) being 1/9 to 9.

2. The water dispersible granule according to claim 1, wherein the granule comprises 1 to 75% by weight of the component (1), 3 to 30% by weight of the total amount of the component (2) and the component (3), and 3 to 90% by weight of the component (4), and 0.1 to 40% by weight of the component (5).

3. The water dispersible granule according to claim 1 or 2, wherein the component (4) is a succharide.

4. The water dispersible granule according to claim 1 or 2, wherein the component (4) is sucrose.

5. The water dispersible granule according to claim 1 or 2 wherein the component (5) is bentonite.

6. The water dispersible granule according to claim 3 wherein the component (5) in bentonite.

7. The water dispersible granule according to claim 4 wherein the component (5) is bentonite.

8. The water dispersible granule according to claim 1, wherein the copolymer of maleic anhydride and diisobutylene is one having a weight mean molecular weight ranging from 500 to 50,000.

* * * * *